United States Patent
Bydlon et al.

(10) Patent No.: US 6,454,746 B1
(45) Date of Patent: Sep. 24, 2002

(54) MEDICATION DELIVERY APPARATUS

(75) Inventors: Roland Joseph Bydlon, Indianapolis, IN (US); Douglas David Hansel, Westerville, OH (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 08/868,774

(22) Filed: Jun. 4, 1997

(51) Int. Cl.$^7$ .............................................. A61M 5/315
(52) U.S. Cl. ...................................... 604/227; 604/232
(58) Field of Search ........................... 604/68, 71, 131, 604/132–135, 140–141, 148, 181, 187, 186, 192, 197, 200, 218, 207–211, 220, 232, 263, 227; 401/6

(56) References Cited

U.S. PATENT DOCUMENTS

| | | | |
|---|---|---|---|
| 1,598,873 A | * 9/1926 | Peterson ........................ 401/6 |
| 2,754,818 A | 7/1956 | Scherer |
| 3,656,472 A | * 4/1972 | Ber Moura ................. 604/157 |
| 4,314,556 A | 2/1982 | Ma et al. |
| 4,710,178 A | 12/1987 | Leonard et al. |
| 4,820,287 A | 4/1989 | Leonard |
| 4,822,340 A | * 4/1989 | Kamstra ..................... 604/135 |
| 4,973,318 A | 11/1990 | Holm et al. |
| D323,030 S | 1/1992 | Ahlstrand et al. |
| D323,031 S | 1/1992 | Ahlstrand et al. |
| D324,423 S | 3/1992 | Ahlstrand et al. |
| 5,092,842 A | 3/1992 | Bechtold et al. |
| D330,079 S | 10/1992 | Dalling et al. |
| 5,279,586 A | * 1/1994 | Balkwill ..................... 604/207 |
| D351,466 S | 10/1994 | Stringer et al. |
| 5,383,865 A | 1/1995 | Michel |
| D360,462 S | 7/1995 | Armbruster et al. |
| 5,514,097 A | 5/1996 | Knauer |
| 5,593,388 A | * 1/1997 | Phillips ....................... 604/135 |
| 5,595,566 A | * 1/1997 | Vallelunga .................. 604/197 |
| 5,611,784 A | * 3/1997 | Barresi et al. ............... 604/211 |
| 5,645,536 A | * 7/1997 | Whisson ..................... 604/200 |
| 5,688,251 A | * 11/1997 | Chanoch ..................... 604/208 |
| 5,728,074 A | * 3/1998 | Castellano et al. ......... 604/207 |
| 5,833,668 A | * 11/1998 | Aguilar ....................... 604/227 |

FOREIGN PATENT DOCUMENTS

| | | |
|---|---|---|
| EP | 0 372 892 | 6/1990 |
| GB | 1198214 | 7/1970 |
| WO | 94/13347 | 6/1994 |

OTHER PUBLICATIONS

Instruction Manual for the BerliPen R injection device.*
Instruction Mannual for the BerliPen® injection device.

* cited by examiner

Primary Examiner—Angela D. Sykes
Assistant Examiner—LoAn H. Thanh
(74) Attorney, Agent, or Firm—Michael T. Bates (57) ABSTRACT

A medication delivery apparatus including a housing, a container of medication mounted to the housing, an outlet such as an injection needle, and a drive assembly adapted to force medication from the container and through the outlet upon movement of an actuator. The housing periphery includes a projecting abutment for digit engagement which is ergonomically designed for abutting contact by a first digit of a hand of a user when the housing is grasped within the user's hand such that a second digit of the hand of the user may operate the actuator. When the actuator is moved axially, this abutting contact of the first digit with the abutment permits application of an axial force by the first digit on the abutment in a direction generally opposite to an axial force applied to move the actuator. As this user applied force on the abutment reduces the amount of frictional force required to be applied by the user on the apparatus housing to counteract the force applied to the actuator during medication delivery, the apparatus housing may be gripped less tightly during use. The housing also is provided with a gripping layer on its periphery formed of a soft touch material.

14 Claims, 6 Drawing Sheets

MEDICATION DELIVERY APPARATUS

BACKGROUND OF THE INVENTION

The present invention pertains to medication dispensing devices, and, in particular, to a portable injector apparatus that permits a user to self-inject medicine such as insulin.

Patients suffering from diseases such as diabetes frequently must inject themselves with insulin solutions. To permit a diabetic to conveniently and accurately self-administer proper doses of insulin, a variety of insulin injector pens have been developed. These insulin pens are so named due to their general resemblance to a writing instrument in their elongated shape and overall length.

An insulin pen typically includes an insulin filled cartridge connected with a needle through which insulin may be injected into a user. Needleless insulin pens are also available. To inject a dosed quantity of insulin, the pen is maneuvered such that the tip of the needle is inserted subcutaneously into the user. Next, in order to move a plunger within the cartridge axially toward the injection needle to force insulin from the cartridge and out through the needle, a button or knob that projects from the distal end of the pen body is depressed and moved relative to the pen body. This knob is typically depressed in line with and toward the needle by a finger, such as the thumb, of the hand in which the insulin pen is being held. In order to so drive the knob, an axial force must be applied to the insulin pen knob, and unless a counteracting force is provided by the patient on the insulin pen body, the needle may be driven deeper into the patient's body. Such a deeper needle penetration below the skin surface is undesirable as not only may it potentially result in a delivery of insulin intramuscularly rather than merely subcutaneously, but it also may cause a user to perceive greater pain or discomfort, which in turn may lead to anxiety by the user in performing insulin injections in the future.

One shortcoming of many existing insulin pens results from the infirmities of its potential user. Over time, many diabetics who self administer insulin via these insulin pens suffer a degree of feeling loss within their fingers as a result of the diabetes. Consequently, comfortably gripping an insulin pen sufficiently tightly at various times during its use to allow for proper operation may prove difficult. For example, one known insulin pen comprises a slender, cylindrical body and cap formed of stainless steel. The stainless steel surface of this model, as well as a textured stainless steel surface provided on an alternate, more colorful pen version, possesses a sufficiently low coefficient of friction so as to be relatively slippery to the grip under many operating conditions. As a result, the high squeezing forces with which pens of this type must be clenched within a user's hand to supply enough of a frictional force on the cylindrical pen body to prevent it from slipping through the hand during plunger shifting associated with insulin injection may not be readily achievable by some users. Even if the required force can be applied by a given user, it would be desirable to reduce the necessary gripping force to decrease the effort required to be expended in using the insulin pen.

Grippability deficiencies with respect to some insulin pens also are manifested at times during their use other than injection. For example, separately gripping and then pulling apart a pen cap and body in order to remove the cap to expose the insulin delivering needle may be problematic for some users.

Thus, it would be desirable to provide a medication injecting apparatus that overcomes these and other problems of the prior art.

SUMMARY OF THE INVENTION

The present invention provides a medication delivery apparatus having a housing formed with a soft touch material to promote a ready and comfortable gripping by a user. Preferably, the soft touch material is secured over a more rigid substrate which forms the housing of the device. The medication delivery apparatus may be one of a variety of so-called pen devices including a reusable pen, a disposable pen, or a needleless pen. The apparatus may be designed and configured to deliver any appropriate medication including proteins and peptides such as insulin, human growth hormone, parathyroid hormone, glucagon, etc. The following detailed disclosure of a device for the delivery of insulin is merely illustrative of the present invention.

As used throughout this application, the term "soft touch" generally references the softer, more rubbery and less slick feel characteristics of a material as perceived by a user in comparison to the feel of other materials such as plastics and metals conventionally employed as the exterior housing of medication delivery apparatuses. Such soft touch materials may be defined in a number of ways. For example, a soft touch material includes a material that has a coefficient of friction greater than that of the substrate material over which the soft touch material is secured. In addition, the soft touch material may be identified as being softer than the underlying substrate as measured on the Durometer A and/or Durometer D scale. Also, the thickness of the material can be determinative in promoting a ready and comfortable gripping by the user. For example, certain soft touch materials may appear softer due to the fact that they are applied to the substrate at a greater thickness.

In one embodiment, the soft touch material comprises a thermoplastic elastomer, such as a styrene-butadiene-styrene (SBS) block copolymer, or a styrene-isoprene-styrene (SIS) block copolymer. Other suitable thermoplastic elastomers include polyurethanes and copolyesters and blends of ethylene-propylene copolymers with polypropylene. In addition to thermoplastic elastomers, the soft touch material may comprise other synthetic elastomers such as polyisobutylene, butyl rubber, and polychloroprene. The soft-touch material may include other polymer materials that result in a better and more comfortable grip by the user. Other general categories of soft touch materials, which may or may not overlap with those set forth above include thermoplastic rubbers, polyester or polyurethane elastomers, vinyls, and urethanes.

The present invention further provides a medical delivery apparatus having a housing that is ergonomically contoured to furnish an abutment engageable by a portion of the hand gripping the apparatus during its operation. The abutment serves as an axial stop against which a user may conveniently apply an axial force on the apparatus to counteract the force applied to administer the injection of medication through the needle of the apparatus. In this aspect of the present invention, the housing may or may not include a soft touch material.

In one form thereof, the present invention provides a medication delivery apparatus including a housing elongated in an axial direction, a container of medication mounted to the housing, an outlet in flow communication with the container to receive medication forced therefrom, and a drive assembly including an actuator movable relative to the housing from a first position to a second position. The drive assembly is adapted to interact with the medication container to deliver medication from the container and through the outlet upon movement of the actuator from the first position to the second position. The exterior periphery of the housing includes a projecting abutment for digit engagement which is axially arranged along the housing length for abutting contact by a first digit of a hand of a user when the housing is grasped within the user's hand such that a second digit of the hand of the user may operate the actuator. The abutment includes an ergonomically curved surface contoured to fit the user's first digit.

In another form thereof, the present invention provides a medication delivery apparatus including a housing elongated in an axial direction and comprising a length extending between first and second axial ends. The housing further includes a generally tubular base and a gripping layer covering at least a portion of the base and forming an exterior surface of the housing. The gripping layer is formed from a material that is softer than the material used to form the portion of the base covered by the gripping layer. The apparatus also includes a container of medication mounted to the housing, an outlet in flow communication with the container to receive medication forced therefrom, a drive assembly, and a dosage member. The drive assembly includes an actuator movable relative to the housing from a first position to a second position and is adapted to interact with the medication container to deliver medication from the container and through the outlet upon movement of the actuator from the first position to the second position. The dosage member is operable to control a quantity of medication delivered from the container by the drive assembly.

In still another form thereof, the present invention provides a housing for a medication delivery device including a medication delivery outlet, a medication filled chamber, and a drive assembly for forcing medication from the chamber through the outlet. The housing includes a body comprising at least one opening through which the drive assembly extends to enable its control, and a cap comprising an interior cavity sized to cover the outlet when the cap is connected with the body. The exterior periphery of the body comprises a soft-touch construction for facilitating gripping of the body by a user upon delivery of the medication.

One advantage of the medication injecting apparatus of the present invention is that the soft touch construction of its periphery results in an instrument which feels comfortable in the hand of a user and which provides a more easily grippable surface.

Another advantage of the present invention is that the laterally projecting, contoured portion of the housing provides a stop surface against which a hand abuts when the apparatus is held for injection, thereby aiding users with limited gripping abilities to more easily resist axial forces applied to the apparatus during a plunging stroke used to effect medication injection.

Still another advantage of the present invention is that the soft touch construction of both the housing body and cap makes it easier for a user to uncap the apparatus to expose the needle for injection.

DESCRIPTION OF THE PREFERRED EMBODIMENTS

Figure 1:
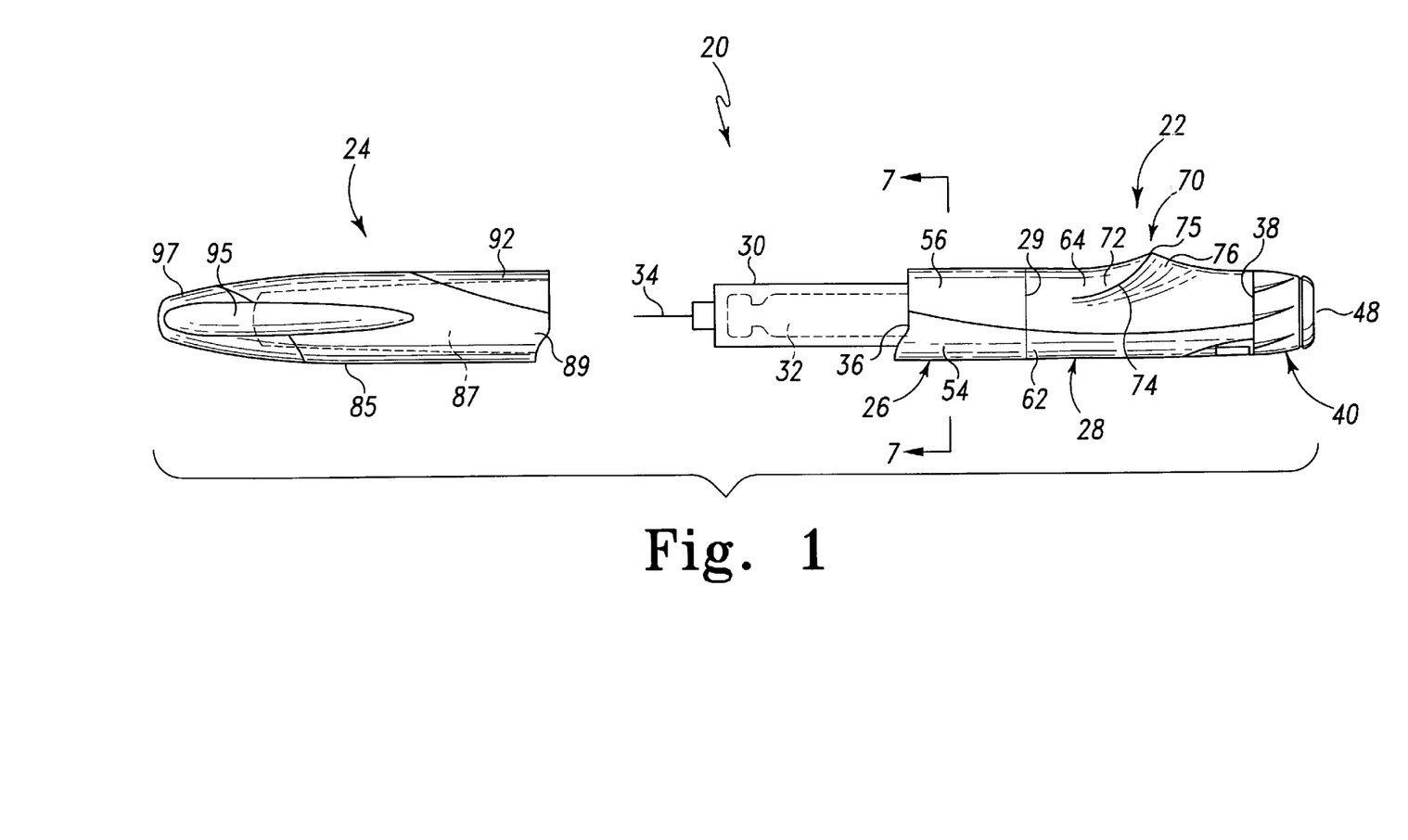
FIG. 1 is a front elevational view of an exemplary embodiment of a medication injecting apparatus in accordance with the principles of the present invention, wherein the injector cap is shown separated from the injector body.

Referring now to FIG. 1, there is shown a partially diagrammatic front view of an insulin injecting apparatus or pen for subcutaneous injection, generally designated 20, arranged in its uncapped state. FIGS. 2–5 show various other views of insulin pen 20 in a capped state or storage state, and FIG. 5 also illustrates the configuration of the capped pen after an injection dosage has been selected. Although shown and described herein with reference to insulin pens, it will be appreciated that this usage is merely illustrative of the present invention and not intended to be limiting. The present invention advantageously may be incorporated into other types of injection apparatus known in the art, such as those employed in the administration of needleless or intramuscular injections.

Insulin pen 20 generally includes an injector body 22 and an injector cap 24. Cap 24 is attachable to the injector body 22 to protect an assembled injection needle during pen storage. The protective, external housing of injector body 22 includes a generally cylindrical, forward axial segment 26 and a rearward axial segment 28 which are fixedly attached together along a parting line indicated at 29 via a solvent bond. An integral construction of the housing portion formed by segments 26 and 28 alternatively may be provided. To facilitate explanation herein, forward and rearward are with reference to injector body 22 with the pen body end at which the needle projects considered as the forward or proximal end and the opposite body end at which pen 20 is dosed and the injection is triggered as described below considered as the rearward or distal end.

Detachably mounted at the forward end 36 of housing segment 26 is a tubular cartridge retainer abstractly shown at 30. A replaceable insulin cartridge indicated in dashed lines at 32 is shown installed within a complementarily shaped interior chamber of cartridge retainer 30. Cartridge 32 is insertable into retainer 30 when retainer 30 is detached from housing segment 26. An injection needle indicated at 34 and through which insulin may be injected into a user is in flow communication with cartridge 32.

Retainer 30 is generally a cylindrical tube with axially extending lugs (not shown) which insert into complementary recesses (not shown) formed in the inner radial periphery of housing segment 26 and which upon retainer rotation are releasably secured thereat to prevent inadvertent axial removal of retainer 30. Retainer 30 may be formed of a clear plastic material, or from an opaque plastic material with suitable windows, to allow visual inspection of the level of the insulin in cartridge 32. With suitable modifications to housing segment 26 and/or cartridge 32, rather than being mounted to the housing via retainer 30, an insulin cartridge 32 may be mounted directly to housing segment 26 in alternate embodiments. Needle 34 is part of an assembly having a base (not shown) which threadedly mounts to the proximal end of cartridge retainer 30. Needle 34 may be mounted in other fashions or directly to the proximal end of cartridge 32.

Figure 5:
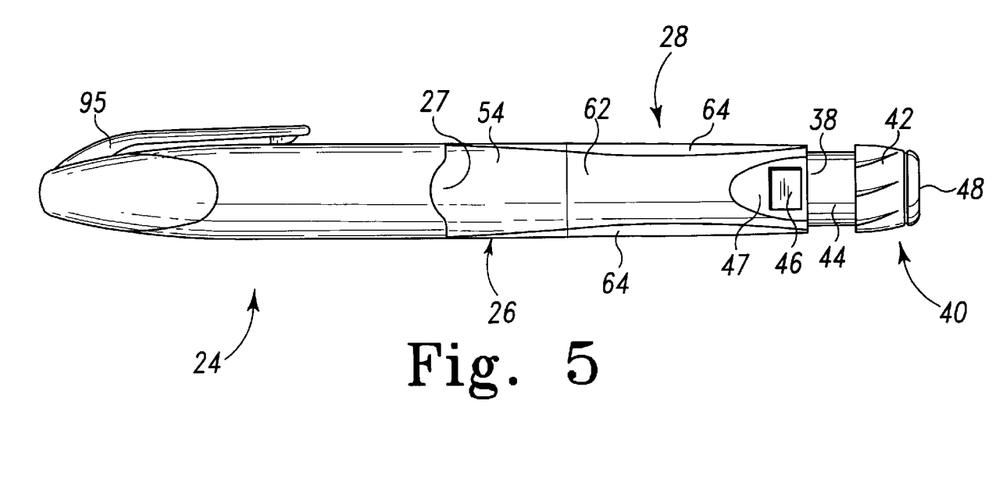
FIG. 5 is a bottom plan view of the medication injecting apparatus of FIG. 2 after being manipulated to select a dosing of its injectable medicine.

With primary reference to FIG. 5, disposed at the distal end 38 of rearward axial segment 28 is a dosage knob, generally designated 40, used to adjust the quantity of insulin to be dispensed per injection. Knob portion 42 is grippable and rotatable in a clockwise direction from the perspective of a FIG. 3 viewer to measure a desired dosage of insulin to be injected upon depression or pushing of actuator button 48. During this rotation to effect dosing, dosage knob 40 also translates in an axial direction away from housing segment 28, such as to the position shown in FIG. 5. A reduced diameter knob portion sleeve 44 rotationally fixed with knob portion 42 and which telescopingly fits within the distal end of housing segment 28 spans the axial space formed between knob portion 42 and distal end 38 during pen dosing. The dialed dosage is provided on a display visible to a user through viewing window 46 covered by a clear plastic cover 47. Finger-engageable actuator button 48, which is free to rotate relative to dosage knob 40, is operatively connected with knob 40 to the other elements of an injector assembly housed within injector body 22 which is utilized to force insulin from cartridge 32 through needle 34. Any of the various assemblies known in the art which converts an input of a plunging or axial force on an externally accessible pen element, such as button 48, into a discharge of insulin from cartridge 32, typically via the axial movement of a not shown plunger within the distal end of cartridge 32, may be employed within the scope of the invention.

The internal structure of assemblies of this type that convert an input or plunging force from an actuator into a discharge of medication from a cartridge are known in the art, and are not further illustrated herein. An example of such an assembly is provided in European Patent Publication No. 730876A2, incorporated herein by reference. Additionally, the present invention is applicable to auto injectors.

Figure 7:
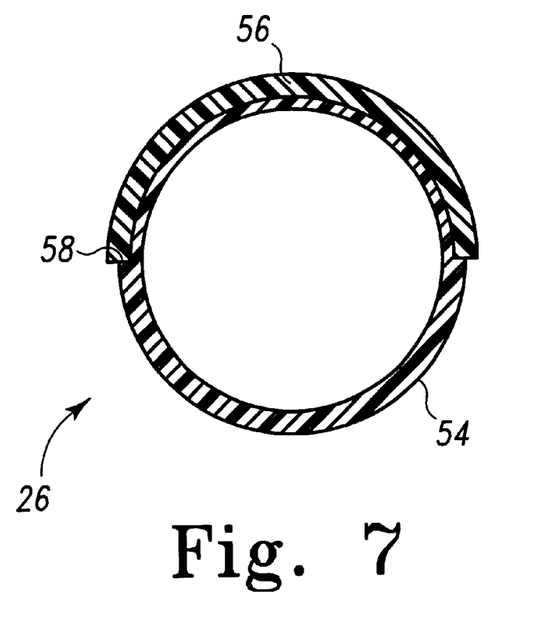
FIG. 7 is a cross-sectional view, taken along line 7—7 of FIG. 1, wherein the pen internal componentry and the housing cap are not shown for purposes of illustration.

The housing of injector body 22 is shaped and constructed to make comfortable the gripping of insulin pen 20 at various times during its use. Forward axial segment 26 has a substantially cylindrical exterior shape along its entire axial length. As further shown in the transverse cross-sectional view of the housing in FIG. 7, axial segment 26 comprises a tubular base or substrate 54 made of a sturdy, relatively stiff material. The wall thickness of base 54 is selected based on the material of construction and, except for recess or depression 58, is generally uniform around the base circumference. Part of the circumference of base 54 is covered by a thin layer or covering 56 of a material which is softer to the touch than the material of substrate 54. Covering 56 nests within radial recess 58, which is provided in the outer diameter of base 54 along its entire length, and protrudes slightly radially beyond the non-recessed region of base 54. Recess 58 allows a thicker layer 56 to be attached to base 54 without having an objectionable step-up from base 54 to layer 56, and further aids in preventing delamination of covering 56 from base 54. As best shown in FIG. 1, different portions of the base circumference are covered by layer 56 along the axial length of segment 26 to achieve an aesthetically pleasing, gentle curve of the edges of layer 56. Covering 56 is preferably formed from a soft-touch material.

Rearward axial segment 28 is formed from a tubular base or substrate 62 with a soft touch covering 64 which nests within a peripheral recess (not shown) in substrate 62 similar to recess 58 of tubular substrate 54. Covering 56 extends the entire axial length of housing segment 28, but covers different circumferential portions along the length as shown to provide an aesthetically pleasing design. In alternate embodiments, different portions, as well as substantially all, of the outer radial periphery of segment 28 may be overlaid with the soft touch covering.

Along a medial portion of its length, housing segment 28 includes a laterally projecting region which forms an abutment, generally designated 70, that enables a user to more readily resist plunging forces applied to button 48 during use of injector body 22. Abutment 70, which at its maximum extends around about thirty-five percent of the housing circumference, includes a forward surface 72 and a rearward surface 76 separated by a crest portion 74. In the rearward direction, or from left to right in FIG. 1, forward surface 72 slopes radially outward from the generally cylindrical portion of housing segment 28 that is adjacent thereto to crest 74. Forward surface 72 is ergonomically contoured to comfortably fit a user's finger so as to serve as a stop surface against which axial forces may be applied during insulin injection as described further below. In the rearward direction, rearward surface 76 slopes radially inward from crest 74 to the adjacent cylindrical housing portion. Rearward surface 76 serves as a stop surface against which a finger may apply an axial force during subcutaneous insertion of needle 34 as described further below.

Figure 2:
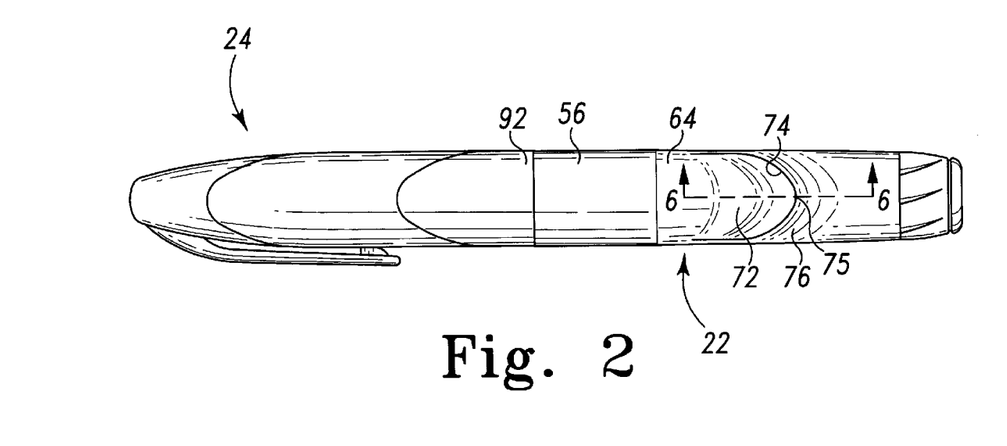
FIG. 2 is a top plan view of the medication injecting apparatus of FIG. 1, wherein the apparatus is arranged in its capped state.
Figure 3:
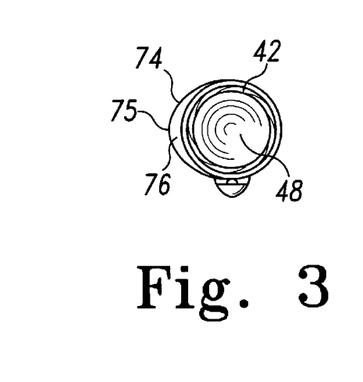
FIG. 3 is a right end view of the medication injecting apparatus of FIG. 2.
Figure 4:
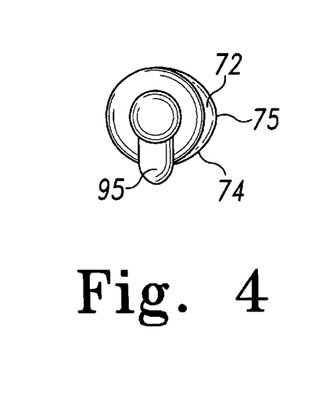
FIG. 4 is a left end view of the medication injecting apparatus of FIG. 2.
Figure 6:
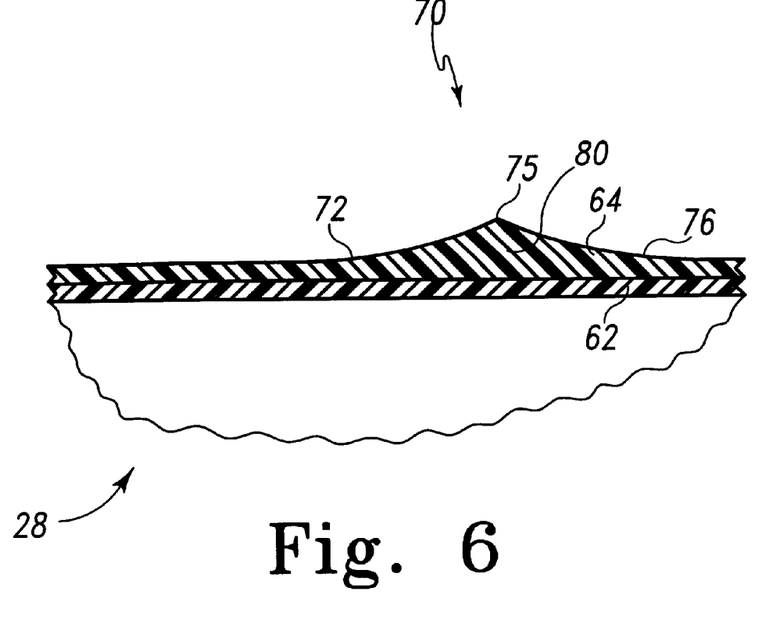
FIG. 6 is a partial, cross-sectional front view of the injector body housing taken along line 6—6 of FIG. 2 further illustrating the finger-engageable abutment of the medication injecting apparatus, and wherein the internal componentry protected within the housing is not shown for purposes of illustration.

As shown in the longitudinal cross-sectional view of FIG. 6 which is taken through the radial peak 75 of crest 74 and along the line of symmetry of abutment 70, both forward and rearward surfaces 72 and 76 are uniformly concave along their respective axial lengths. Along this cross-section, forward surface 72 has a constant radius of curvature of approximately 1.544 inches, and rearward surface 76 has a constant radius of curvature of approximately 0.775 inch. Curvatures different from those shown may be provided along the line of symmetry as well as other regions of the pen circumference constituting abutment 70 within the scope of the invention. The curvatures of surfaces 72 and 76 each vary around the pen circumference to provide gradual slopes to these surfaces such that crest 74, as shown in the top view of FIG. 2, is substantially horseshoe in shape and oriented non-transversely to the longitudinal axis of injector body 22. At radial peak 75 of crest 74, rearward axial segment 28 has its maximum diameter of about 0.90 inch, which is about 0.10 inch larger than the diameter of the portions of the housing axially adjacent abutment 70. As considered from the perspective of a FIG. 3 viewer, the profile of each portion of crest 74 that extends from the forward crest end to the rearward crest portion positioned along the line of symmetry of abutment 70, has a radius of curvature of about 0.419 inch.

As shown in FIG. 6, abutment 70 comprises a laterally projecting portion 80 of the soft touch layer 64. In alternate embodiments where a harder and less pliable abutment construction is required, the portion of the substrate underlying the abutment may be provided with a protuberance or a series of fins having the same overall geometry as abutment 70, and the soft touch layer covering that protuberance may have the same thickness as provided over the other covered regions of housing segment 28.

Abutment 70 is spaced from the distal end 38 of the pen housing and from button 48 a sufficient distance to suit the physical dimensions of a wide variety of users. In the shown embodiment, peak 75 of crest 74 is spaced about 1.29 inches from the distal face of actuator button 48 when fully depressed. Other similarly measured spacings may alternatively be provided. Dosage knob 40 is structured to axially move rearwardly from distal end 38 about 0 inch to about 1.20 inch in 0.02 inch increments when knob 40 is dialed to measure insulin quantities ranging from 0 units to a maximum dosage of 60 units in single unit increments One suitable material for tubular bases 54 and 62 is a synthetic thermoplastic resin, particularly an ABS polycarbonate alloy known as Triax® available from Bayer Corporation of Pittsburgh, Pa. One suitable grade of Triax is Triax 2153 which has a hardness of 113 on the Rockwell scale. In one embodiment, the non-recessed portions of the bases for Triax® has a thickness of approximately 0.15 inch. Other base materials, including other types of plastics and metals such as a thermoplastic PC/PBT alloy known as Xenoy® resin available from General Electric Plastics of Pittsfield, Mass., and a thermoplastic polymer alloy known as Makroblend available from Bayer Corp. may be used.

One suitable soft touch material for coverings 56 and 64 is a thermoplastic elastomer, such as a styrene-butadiene-styrene (SBS) block copolymer, or a styrene-isoprene-styrene (SIS) block copolymer. Other suitable thermoplastic elastomers include polyurethanes and copolyesters and blends of ethylene-propylene copolymers with polypropylene. In addition to thermoplastic elastomers, the soft-touch material may comprise other synthetic elastomers such as polyisobutylene, butyl rubber, and polychloroprene. The soft touch material may include other polymer materials that result in a better and more comfortable grip by the user. The polymers listed above are only examples of numerous materials that can be utilized as long as the material is soft to the touch.

More specifically, one suitable soft touch material is a polyester elastomer known as Hytrel® available from DuPont Engineering Polymers of Wilmington, Del. This particular product is a butylene/poly(alkylene ether) phthalate. Other suitable soft touch materials include a copolyester/polycarbonate alloy known as Ektar® available from Eastman Chemical Company of Kingsport, Tenn., a thermoplastic elastomer known as Sarlink® available from Novacor Chemicals Ltd. of Clagary, Alberta, Canada, and a copolyester/polycarbonate known as Eastalloy® available from Eastman Chemical Company. Still another suitable thermoplastic elastomer is known as Santoprene®, available from Advanced Elastomer Systems of Newport, Wales, United Kingdom. Yet another suitable thermoplastic elastomer is Kraton®, available from Shell Chemical Co. of Houston, Tex. The above polymers are produced in various grades with varying associated hardness levels.

In one embodiment, recess 58 and the recess in substrate 62 each have a radial depth of about ten thousandths (0.0010) inch, and coverings 56 and 64 are each formed with a thickness of about twenty-five thousandths (0.0025) inch. In this embodiment, a preferred material for coverings 56 and 64 is a specialty grade of Hytrel® known as Hytrel® 3078. Hytrel® 3078, which has a hardness of 30 on the D-scale durometer and a flexural modulus of 4000 psi furnishes comfortable feel properties to insulin pen 20.

Other materials having hardnesses up to about 50 on the D-durometer scale may be suitable soft touch materials. However, it is possible that plastics having a hardness greater than 50 on the D-durometer scale may have characteristics of a soft touch feel based primarily on the coefficient of friction of such material.

Housing segments 26 and 28 are each formed via injection molding, preferably via a two-shot molding or co-injection molding process. This fabrication technique permits a chemical bonding to occur between the Triax® and Hytrel® materials used for the tubular bases and soft-touch layers, respectively. This chemical bonding ensures a secure interconnection at each of the interfaces of the base and soft-touch layer. The soft touch layers may be attached to their respective bases in alternate fashions. For example, a soft touch layer and base may be adhesively attached together, or mechanically secured together with interlocking fasteners such as plugs and cooperating recesses integrally molded into the parts. Knob 40 is also provided with a soft-touch periphery on knob portion 42 in order to make it more comfortable to grip and rotate during its operation. Knob 40 is injection molded from an ABS plastic and the soft touch material is insert molded in an injection molding process over the outer periphery of knob portion 42. Injector cap 24 includes a main housing body 85 with an interior cavity, indicated in dashed lines at 87, that opens out to pen cap end 89. Cap 24 includes a curved edge that interfaces with a curved camming portion 27 (see FIG. 5) of forward axial segment 26. This curved interface results in injector cap 24 being registered with injector body 22 during attachment to align any designs on the pen periphery, and further results in rotation of injector body 22 relative to injector cap 24 automatically camming cap 24 out of its attached engagement with injector body 22. Cavity 87 is sized to accommodate cartridge retainer 30 and needle 34 when insulin pen 20 is assembled into the arrangement shown in FIG. 2. The interior periphery of housing body 85 defining cavity 87 and proximate cap end 89 is complimentarily shaped with the proximal end of cartridge retainer 30 so as to provide for a snap-fit attachment of cap 24 to injector body 22 to prevent inadvertent cap removal. In alternate embodiments, housing body 85 may attach directly to the housing segment 26 of injector body 22. Housing body 85 includes a soft touch covering 92. Covering 92 is formed with the same thickness as cover 56 of body housing segment 26, and fits within a radial recess in body 85. The main housing body 85 and the portion of cartridge retainer 30 to which cap 24 attaches are keyed such that soft-touch covering 92 is aligned with covering 56 on housing segment 26 as shown in FIG. 2 when injector cap 24 is attached to injector body 22.

A resilient pocket or fastening clip 95 is integrally formed with a plastic collar portion 97 that includes a socket into which the proximal end of housing body 85 inserts. Collar 97 is permanently secured via solvent bond or sonic welding to housing body 85. Clip 95 extends in a direction opposite to the direction in which needle 34 projects, such that when pen 20 is slipped into a pocket with clip 95 fitting over the edge of the pocket, needle 34 is pointed upward so as to prevent any insulin from draining therefrom by gravity. Cap housing body 85 and soft touch covering 92 are formed of the same materials and in the same injection molding process as the tubular base 54 and covering 56 of injector body housing segment 26.

The structure of insulin pen 20 will be further understood in view of the following explanation of its ordinary operation by a user. With insulin pen 20 arranged in its capped state as shown in FIG. 2, a user prepares for injection by first dialing knob 40 to obtain the proper dosage. In particular, dosage knob 40 is rotated until the measured quantity indicated through viewing window 46 equals the required insulin dose. Next, injector cap 24 is removed from injector body 22. This cap removal step may be performed prior to the dosing step, if desired. During cap 24 removal, a user may grasp injector cap 24 at soft-touch covering 92, and grasp injector body 22 at covering 56 or 64. The soft-touch material on both of the parts being separated makes it easier for a user to grip and then rotate the parts relative to one another to remove injector cap 24. In an alternate design lacking the cap camming feature, the soft-touch coverings of injector cap 24 and injector body 22 facilitate their gripping to allow cap 24 to be pulled from body 22.

Next, provided a needle 34 is assembled as shown in FIG. 1, the user maneuvers the injector body 22 such that needle 34 is inserted subcutaneously into, for example, her arm or leg. During this needle insertion, a user may grasp and hold injector body 22 within her clenched hand such that the side of a finger abuts stop surface 76. Alternatively, a user may grip and hold pen 20 within the ends of her fingers such that the tip of one or more fingers is pressed against rear stop surface 76. The engagement of stop surface 76 allows a user to provide an axial force on abutment 70 with her finger which is transferred to the pen housing and therefore to the needle to achieve the skin penetration.

Figure 8:
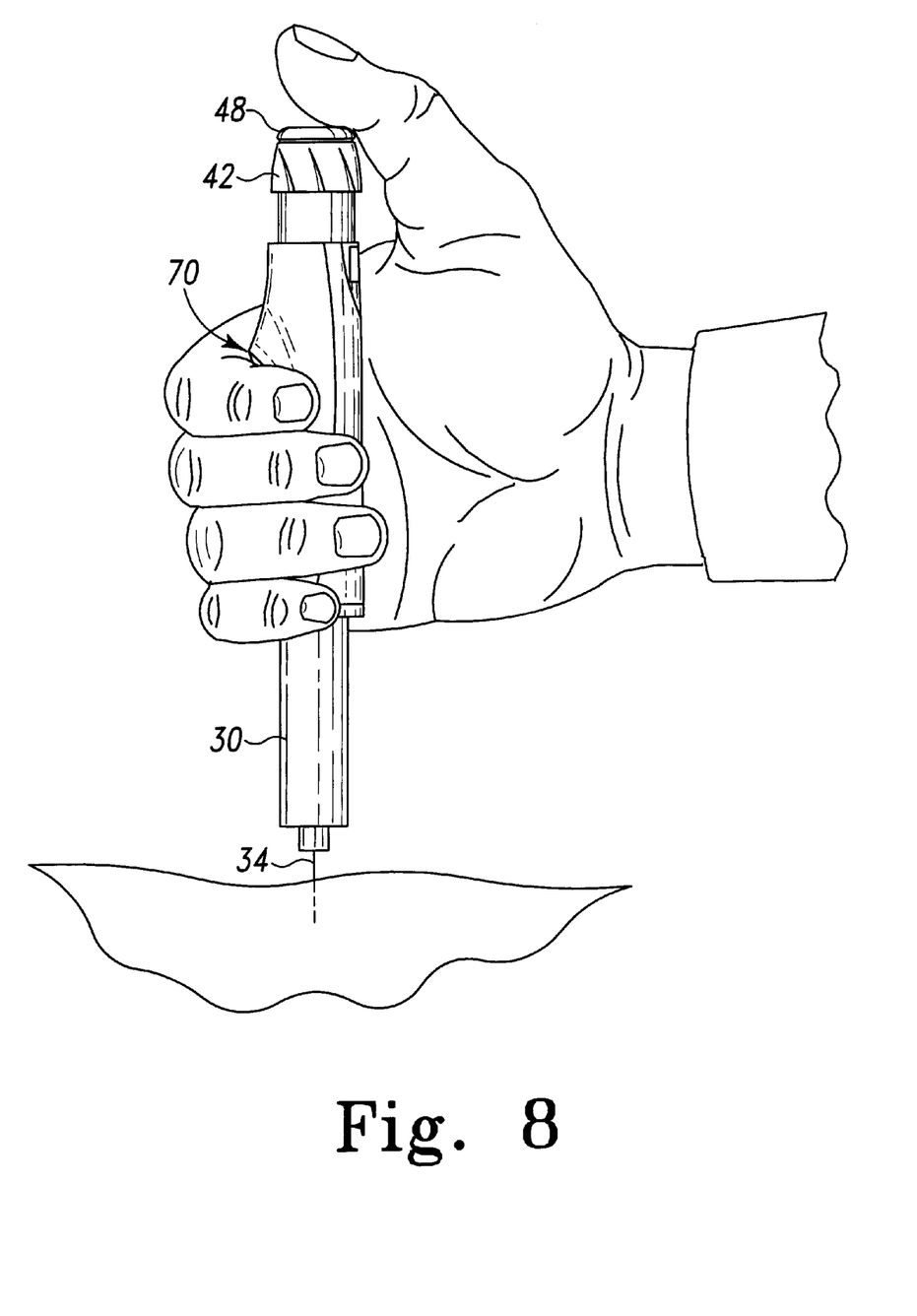
FIG. 8 is a perspective view of the injector body of the medication injecting apparatus of FIG. 1 being used by a person to self-inject medicine.

After needle 34 is so inserted, the user may grasp injector body 22 within her hand such that the side of a finger, typically the index finger, will press into contact with forward stop surface 72, and such that her thumb is positionable upon actuator button 48. When the user's hand is so arranged, the insulin pen 20 is being held as shown in the illustration of FIG. 8. Then, a user may use her thumb to depress or plunge actuator button 48 to inject the insulin dose. It will be appreciated that during depressing and moving of button 48 relative to the remainder of injector body 22, an axial force in opposition to the force applied to button 48 must be applied to injector body 22 to avoid driving needle 34 further under the skin. Because the user's finger contacts a generally axially facing portion of abutment 70, namely stop surface 72, an axially directed force in opposition to the force applied by the thumb on button 48 may be applied on injector body 22 by the side of the finger. Any force so applied on abutment 70 reduces the amount of frictional force required to be applied on the housing by way of a clenching of injector body 22. After the actuator button has been plunged, the user, while still holding the pen as shown in the arrangement of FIG. 8, then may lift pen 20 to withdraw needle 34, remove and replace needle 34, and cap pen 20 for later use.

Figure 9:
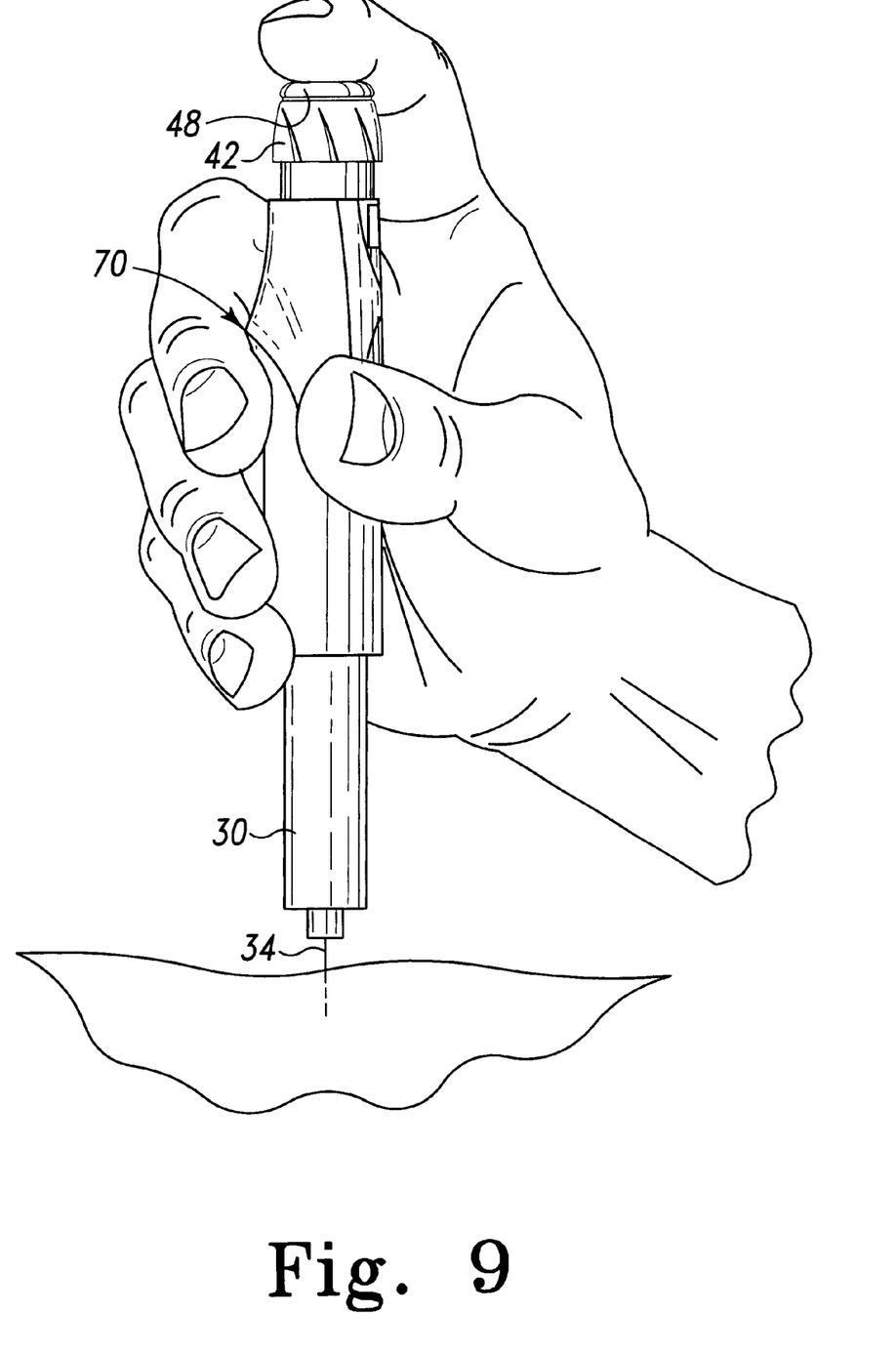
FIG. 9 is a perspective view of the injector body of the medication injecting apparatus of FIG. 1 being held by a person in a manner different from its handling in FIG. 8 during the self-injection of medicine.

The configuration of insulin pen 20 is adapted to enable its handling by users in different manners than shown in FIG. 8. In FIG. 9, there is shown a perspective view of insulin pen 20 being gripped to allow an index finger plunging of the button 48 to discharge insulin through the inserted needle. The user's middle finger fits onto abutment 70, and a generally axial force may be applied on the abutment 70 by the side of that finger to counter a force being applied by the index finger to cause insulin injection. Although not illustrated, the user may use her middle finger to press button 48, in which case the third finger would fit onto abutment 70. Furthermore, it is possible to grasp insulin pen 20 in such a way that that the thumb fits onto abutment 70 and one of the fingers is used to press button 48.

Figure 10:
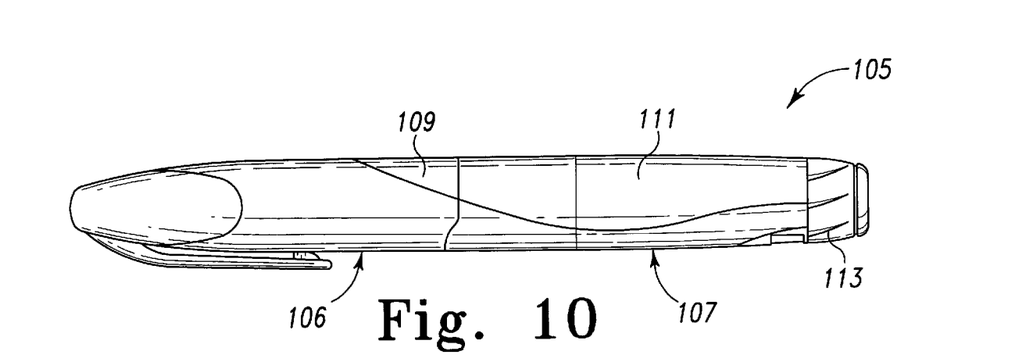
FIG. 10 is a front elevational view of a second embodiment of a medication injecting apparatus of the present invention.
Figure 11:
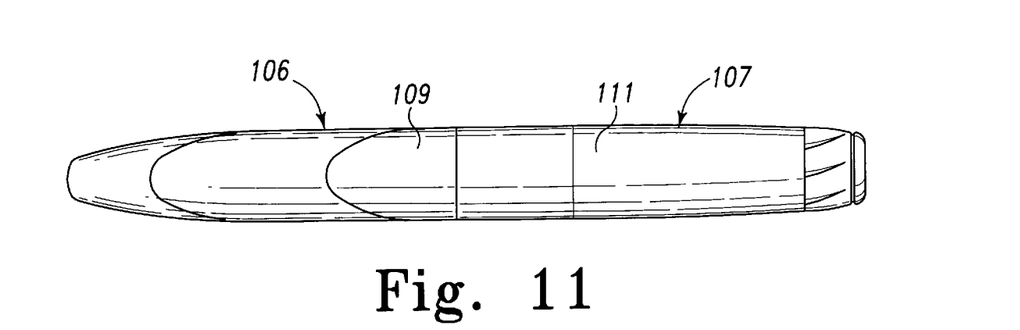
FIG. 11 is a top plan view of the medication injecting apparatus of FIG. 10.
Figure 12:
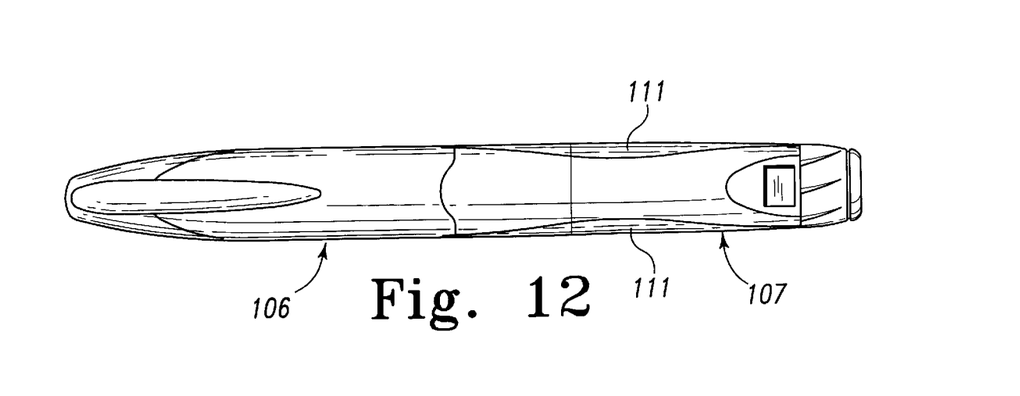
FIG. 12 is a bottom plan view of the medication injecting apparatus of FIG. 10.

Referring now to FIGS. 10 through 12, there is respectively shown a front view, a top view and a bottom view of an alternate embodiment of an insulin pen of the present invention shown in its capped state. Insulin pen 105 is substantially similar to insulin pen 20 in all material respects including construction shapes and materials, with the primary exception being that no finger-engagable abutment is provided on the housing of injector body 107. To provide desirable grip characteristics, soft-touch coverings 109, 111 are provided on portions of the exterior peripheries of injector cap 106 and injector body 107, respectively. Knob portion 113 is also furnished with a soft-touch covering.

While this invention has been shown and described as having multiple designs, the present invention may be further modified within the spirit and scope of this disclosure. For example, the soft-touch cover material and/or the finger-engagable axial abutment may be furnished on a sleeve which retrofits existing medication delivery pens. In addition, the soft touch cover material and abutment may be used with needleless injectors. This application is therefore intended to cover any variations, uses, or adaptations of the invention using its general principles. Further, this application is intended to cover such departures from the present disclosure as come within known or customary practice in the art to which this invention pertains.

What is claimed is:

1. A medication delivery apparatus comprising:
   a housing elongated in an axial direction and having a length extending between forward and rearward axial ends, said housing comprising a generally tubular base and a gripping layer covering at least a portion of said base, said gripping layer being formed from a material that is softer than a material used to form the portion of said base covered by said gripping layer;
   a container of medication mounted to said housing;
   an outlet in flow communication with said container to receive medication forced therefrom, said outlet disposed closer to the forward axial end of said housing than the rearward axial end;
   a drive assembly comprising an actuator movable relative to said housing from a first position to a second position, said drive assembly operatively associated with said container to deliver dosed quantities of medication from said container and through said outlet upon movement of said actuator from said first position to said second position; and
   said gripping layer comprising a projecting abutment for digit engagement, said abutment being axially arranged along said housing length for abutting contact by a first digit of a hand of a user when said housing is grasped within the hand of the user such that a second digit of the hand of the user may operate said actuator, said abutment comprising an ergonomically curved surface contoured to fit the user's first digit.

2. The medication delivery apparatus of claim 1 wherein said abutment comprises a crest portion at an axial end of said ergonomically curved surface, said ergonomically curved surface being axially disposed between said crest portion and said forward axial end of said housing.

3. The medication delivery apparatus of claim 2 wherein said ergonomically curved surface is generally concave.

4. The medication delivery apparatus of claim 2 wherein said crest portion is configured in a generally horseshoe shape and arranged non-perpendicular to said axial direction.

5. The medication delivery apparatus of claim 1 wherein said outlet comprises a needle, wherein along its axial length said abutment sequentially comprises said ergonomically curved surface, a crest portion and a stop surface, said stop surface axially disposed between said crest portion and said rearward axial end of said housing, wherein said ergonomically curved surface slopes radially outward from said generally tubular base to said crest portion, and wherein said stop surface slopes radially inward from said crest portion to said generally tubular base, said stop surface abuttable by a digit of a hand of a user to receive an axial force on said housing when said housing is gripped by the user during insertion of said needle into a user.

6. The medication delivery apparatus of claim 5 wherein said stop surface comprises a concave ergonomically curved surface.

7. The medication delivery apparatus of claim 5 wherein said ergonomically curved surface comprises a longer axial length than said stop surface.

8. The medication delivery apparatus of claim 1 wherein said material forming said gripping layer comprises a thermoplastic elastomer.

9. The medication delivery apparatus of claim 1 wherein said abutment is formed by an increased thickness of said gripping layer.

10. The medication delivery apparatus of claim 1 wherein said outlet comprises an injection needle, and further comprising a housing cap including an interior cavity sized to accommodate said injection needle when said housing cap is connected with said housing, said cap comprising a fastening clip.

11. A medication delivery apparatus comprising:
a housing elongated in an axial direction and comprising forward and rearward axial ends, said housing further comprising a generally tubular base and a gripping layer, said gripping layer covering at least a portion of said base and extending the entire axial length of said housing, said gripping layer being formed from a material that is softer than a material used to form the portion of said base covered by said gripping layer;
a container of medication mounted to said housing;
an outlet in flow communication with said container to receive medication forced therefrom; and
a drive assembly comprising an actuator, said actuator advanceable toward said housing in said axial direction from a first position beyond said forward axial end of said housing to a second position, said drive assembly operatively connected with said container to force a dosed quantity of medication from said container and through said outlet upon movement of said actuator from said first position to said second position; and a dosage member operable to control said dosed quantity of medication delivered from said container by said drive assembly.

12. A housing for a medication delivery apparatus of the type wherein medication is delivered to a user via a needle in communication with medication disposed in a container within said housing, comprising:
a generally tubular base member, said generally tubular base member having an exterior surface and having a length extending between a forward axial end and a rearward axial end, said forward axial end attachable to said needle;
a gripping layer covering at least a portion of said exterior surface, said gripping layer being formed of a material that is softer than a material used to form the portion of the base member covered by said gripping layer, said gripping layer comprising a projecting abutment for digit engagement, said abutment being axially arranged along the length of said base member and comprising an ergonomically curved surface contoured to fit a first digit of a hand of a user when the housing is grasped by a user, and wherein said abutment comprises a crest portion at an axial end of said ergonomically curved surface, said ergonomically curved surface axially disposed between said crest portion and said forward axial end of said base member, said abutment further comprising a stop surface, said stop surface axially disposed between said crest portion and said rearward axial end of said base member, wherein said ergonomically curved surface slopes radially outward from said generally tubular base member to said crest portion, and wherein said stop surface slopes radially inward from said crest portion to said generally tubular base member, said stop surface abuttable by a digit of a hand of a user to receive an axial force on said housing when said housing is gripped by the user during insertion of said needle into a user.

13. The housing of claim 12, wherein said stop surface comprises a concave surface.

14. The housing of claim 13, wherein said ergonomically curved surface comprises a longer axial length than said concave stop surface.

\* \* \* \* \*